United States Patent [19]

Dunlap

[11] 4,321,258
[45] Mar. 23, 1982

[54] NON-TOXIC INSECTICIDE

[76] Inventor: Dorsey S. Dunlap, 136 Elm St., South Williamsport, Pa. 17701

[21] Appl. No.: 177,602

[22] Filed: Aug. 13, 1980

[51] Int. Cl.³ .......................................... A01N 25/00
[52] U.S. Cl. ..................................... 424/84; 424/357
[58] Field of Search .................................. 424/84, 357

[56] References Cited

U.S. PATENT DOCUMENTS 2,303,981  12/1942  Britton et al. .................. 424/357
3,350,264  10/1967  de Lisle ........................... 424/357
4,205,066   5/1980  Hennart et al. .................. 424/84

OTHER PUBLICATIONS

J. Econ. Entomology, vol. 25, pp. 1053–1059; vol. 40, No. 2, pp. 215–219; and vol. 44, No. 6, pp. 891–895.

Primary Examiner—Donald B. Moyer
Attorney, Agent, or Firm—Blair, Brown & Kreten

[57] ABSTRACT

Disclosed herein is a non-toxic composition for mechanically killing insects and the like wherein an attractant for insects is provided and within the attractant there are a plurality of needled particles mixed therewithin so that when the insect encounters the composition the needled particles lacerate the insect.

5 Claims, No Drawings

NON-TOXIC INSECTICIDE

BACKGROUND OF THE INVENTION

Confrontations between man and insect have existed for as long as the two. An attempt to bring insects under man's dominion has been seen to be necessary in order to control food production, the spread of diseases, and in general to make the environment more inhabitable for man.

However, the prior art's involvement in insect control seems to be predominantly one of chemical warfare, the following of which appears to be a typical U.S. Pat. No.: 2,957,804—Shuyler.

It is painfully clear that the use of toxic substances in an effort to reduce the population of vermin and the like is an endeavor played for extremely high stakes. Firstly, it is difficult to selectively dictate what will ingest the toxic substances. Secondly, indescriminate spraying of toxic chemicals on acreage and the like has the undesirable effect of running off into streams and rivers, and the bulk manufacturing and storage of these substances is equally hazardous. Thirdly, many of these agents are petroleum based, the cost of which is rapidly spiraling, to the detriment of our society. Fourthly, these substances do not insure that the vermin will absorb a sufficient amount of the substance to produce the desired lethal effect; the net result being that continuing generations of various species have become immune to certain toxic substances.

By way of contrast, the instant application is directed to and defines a composition which is non-toxic in nature but when encountered by an insect, mechanically kills the insect by laceration. The sizing of the particles which provide the laceration are such that these needles are only harmful to insects themselves, and the other forms of life find the substance in toto harmless.

OBJECTS AND SUMMARY OF THE INVENTION

Accordingly, it is an object of this invention to provide a device which is specific in its ability to eradicate unwanted pests.

It is yet a further object of this invention to provide a device of the character described above which will be lethal to insects as a function of their dimensions, but completely and totally non-lethal to other forms of animal life.

It is yet another object of this invention to provide a device of the character described above which is relatively inexpensive to manufacture and extremely safe to use.

It is yet a further object of this invention to provide a device of the character described above in which the active ingredients for the composition are chemically non-toxic.

These and other objects will be made manifest when considering the following detailed specification.

BRIEF DESCRIPTION OF THE PREFERRED EMBODIMENT

The composition according to the present invention can best be characterized by first defining the effective mechanism by which this composition operates. An attractant is provided which lures the insect thereto, the attractant can be conceivably a desirable food product for the insect, a sexual lure, or any other type of substance that will induce an insect thereto. Thoroughly mixed within the attractant there is provided a plurality of needle-shaped particles of a suitable dimension that are capable of lacerating insects since the needle particles are dimensioned according to their pore sizes. The attractant is provided with a hardening substance whereupon when the insect encounters the attractant an ingredient therein hardens the composition and therefor the needle particles next to the body of the insect. Typically, this hardening takes place in the presence of a liquid such as body moisture of the insect. In an attempt to remove the needle particles away from the body, the insect's rear legs perform a preening operation which actually drives the needle particles into the body fatally. It has been observed that insects, encountering compositions of this type, immediately seek out a source of liquid in an attempt to replenish the body fluids that are being removed by the lacerations, but the composition according to the present invention is so formed that the insect migrating to an additional source of fluid will only aggravate the process by wetting further areas of his body and further affixing the needle-shaped particles to his torso. Moreover, colony behavior patterns among some insects suggest that one or more contaminated insects, should they return to their nest, will contaminate other segments of the population should they attempting to assist in the preening operation in an attempt to help remove the lethal needle particles.

It has been found that one extraordinarily effective source of these needle particles is diatomaceous earth extracted specifically from fresh water. This earth when suitably atomized as through an attrition mill can be appropriately sized so as to be selective for certain insect dimensions.

One suitable source for an attractant has been found to be a sexual stimulant for a specific insect, such as synthesized hormones or naturally occuring hormones and scents emitted by the insects during breeding.

Yet a further effective attractant has been found to be a source of food for the insect which in one form includes sugar, cornstarch, dextrin, dried molasses, and soybean mill feed. Some of the sugars listed above have the property that when encountering moisture, if sufficiently pulverized, will harden against the moistened body, and with the diatomaceous earth uniformly disposed within the sugar particles will provide an irritant for the insect with the net effect that his trying to clean himself of the needle particles will in fact drive the particles deeper within his torso. It has been found that a ratio of attractant to needle particles can range from 90% to 10% by weight or at the other extreme 10% to 90% by weight, respectively.

A specific formulation that is found to be especially compelling to insects consisting essentially of the following by weight:
Fresh Water Diatomaceous Earth: 66%
Attractants: 34%
  Cane Sugar, cornstarch, dextrin: 17%
  Cane molasses, soybean mill feedings: 17%

A particularly beneficial ratio defines that cornstarch and dextrin each comprise 1½% and the cane sugar comprises 14% of the total 17% listed above. Further, it has been found that the powdered cane molasses comprises 14% and the soybean mill feedings comprise 3% of the above referenced ratio.

In order to assure a total complete uniform mixture of the diatamaceous earth throughout the attractant, it is believed to be necessary that all other ingredients are mixed prior to adding the diatamaceous earth.

Further, having thus described the invention, it should be apparent that numerous structural modifications are contemplated as being a part of this invention as set forth herein above and as defined hereinbelow by the claims.

What is claimed is:

1. A composition for mechanically killing insects and the like consisting essentially of:

diatomaceous earth 66% by weight
   cane sugar, cornstarch and dextrin 17% by weight
   cane molasses and soybean mill feedings 17% by weight.

2. The composition in accordance with claim 1 wherein said cornstarch and dextrin each are present in $1\frac{1}{2}$% by weight of the 17% and said cane sugar provides the remaining 14% by weight.

3. The composition in accordance with claim 1 wherein said cane molasses comprises 14% and said soybean mill feedings comprise 3% by weight.

4. The composition in accordance with claim 1 wherein said cane molasses is powdered.

5. The composition of claim 1 wherein said diatomaceous earth is extracted from a fresh water source.

* * * * *